United States Patent [19]

Adams

[11] 4,263,912
[45] Apr. 28, 1981

[54] MILKING APPARATUS AND METHOD

[76] Inventor: Frank H. Adams, 1246 Indiana Ave., Salt Lake City, Utah 84104

[21] Appl. No.: 26,703

[22] Filed: Apr. 3, 1979

Related U.S. Application Data

[63] Continuation of Ser. No. 804,651, Jun. 8, 1977, abandoned, which is a continuation-in-part of Ser. No. 770,342, Feb. 22, 1977, abandoned.

[51] Int. Cl.$^3$ ............................................. A61M 1/06
[52] U.S. Cl. .................................................. 128/281
[58] Field of Search ....................... 128/280, 281, 282; 119/14.52, 14.53

[56] References Cited

U.S. PATENT DOCUMENTS

| 940,454 | 11/1909 | Fowler | 128/281 |
| 2,156,211 | 4/1939 | Van Der Meulen | 119/14.52 |
| 2,542,505 | 2/1951 | Gascoigne | 128/281 |
| 3,782,385 | 1/1974 | Loyd | 128/281 |

FOREIGN PATENT DOCUMENTS

| 524638 | 12/1953 | Belgium | 128/282 |
| 272561 | 3/1951 | Switzerland | 119/14.53 |
| 9747 | of 1894 | United Kingdom | 128/281 |
| 533493 | 2/1941 | United Kingdom | 128/281 |

*Primary Examiner*—Robert W. Michell
*Assistant Examiner*—Arthur S. Rose
*Attorney, Agent, or Firm*—J. Winslow Young; H. Ross Workman; Rick D. Nydegger

[57] ABSTRACT

A milking apparatus and method for improved lactation, the apparatus including means for applying suction to at least the nipple portion of a mammary gland while simultaneously and/or selectively imparting a constrictive, manipulatory force to the nipple and/or the mammary gland adjacent the nipple. An inflatable toroidal member is adapted to be placed in encirclement of the nipple portion of the mammary gland. The manipulatory force is supplied by selectively inflating the inflatable toroidal member. Inflation of the toroid causes an inner wall surface to be distended inwardly thereby imparting a constrictive force to the nipple and/or adjacent, underlying mammary gland. The toroidal member may also be provided with an inner wall thickness which is selectively predetermined so as to be preferentially distended during inflation of the toroidal member. Additionally, compartmentalization of the toroidal member provides a certain degree of mimicry of the normal suckling action of an infant for improved lactation. A peristaltic pumping action is also selectively imparted to the mammary gland and/or nipple by selectively predetermining the inner wall thicknesses along the toroidal surface placed in juxtaposition with the mammary gland.

2 Claims, 8 Drawing Figures

MILKING APPARATUS AND METHOD

This is a continuation of application Ser. No. 804,651, filed June 8, 1977, now abandoned, which is a continuation-in-part application of my copending application Ser. No. 770,342 filed Feb. 22, 1977, now abandoned.

BACKGROUND

1. Field of the Invention

This invention relates to milking apparatus and more particularly to milking apparatus involving a combination suction and manipulatory pumping action for improved lactation.

2. The Prior Art

Milk is an important nutritional component throughout the world. More particularly, human milk is uniquely adapted to the nutritional needs of infants since it is superior to any substitute devised by nutritional scientists. Breast feeding has been found to contribute directly to the infant's immunological adaptation to extrauterine life. Also, human milk is free of hazards associated with artificial feeding, characterized in disadvantaged societies particularly by malnutrition and gastroenteritis, and in affluent societies by obesity, allergic disorders and metabolic derangements including tetany and hyper-osmolar dehydration.

Notwithstanding its biological superiority over any other form of infant feeding, breast feeding has declined in all the technologically advanced societies of the world during this century. Breast feeding is also declining in developing countries with alarming deleterious effects on child health with resultant adverse effects on domestic and national economies. The factors which have contributed to this decline are numerous and complex.

The need for intensifying activities relevant to the promotion of breast feeding has been expressed in numerous documents in recent years particularly since many authorities are convinced that breast milk is the best food for infants. In view of the determination that breast feeding constitutes the most effective safeguard against malnutrition and infection in infancy, particularly in disadvantaged communities, it has been strongly recommended that the promotion of breast feeding be advanced internationally. It is proposed that breast feeding be advanced through educational activities, curtailment of promotion of artificial feeding, improved facilities for working mothers who breast feed, and improved devices for stimulating lactation during periods when infant suckling is inadequate to suitably stimulate appropriate lactation.

With regard to the latter objective, it is currently believed that the presently available devices for stimulating lactation are generally ineffective in many instances and fail to deter loss of production of breast milk. One particular prior art device involves a rigid, frusto-conical surface having a generally bell-shaped configuration. The base of the bell portion is placed over a substantial portion of the breast to seal the breast for the application of suction to at least the nipple. A conventional squeeze bulb is attached to the apex of the bell and, upon release, imparts suction against the portion of the breast enclosed by the bell housing. Numerous women report this device to be uncomfortable and, in certain circumstances, painful to such a degree that further mechanical lactation becomes impossible. With the failure of mechanical lactation and inadequate infant suckling, many women abandon all further attempts at breast feeding.

Cow's milk is the primary source for a wide variety of food products including milk, per se, and is principally supplied by large dairy operations. A conventional dairy operation generally utilizes automatic, suction-type milking devices for extracting a major portion of the milk from the cow's udders. The automatic milking device consists of four cup-like rigid housings with individual elastic sleeves therein. Each elastic sleeve is adapted to be placed over the individual teat of the cow. The elastic sleeve is smaller in diameter than the teat and the elasticity of the same is used to impart a constrictive action to the teat.

This elastic sleeve is referred to in the trade as an "inflation". This term is a misnomer since the sleeve is expanded only by the cyclical application of a negative pressure between the rigid housing and the sleeve. The cyclic expansion of the sleeve by the negative pressure allows milk to flow into the teat. Release of the negative pressure allows the elastic sleeve to return to its unstretched state and thereby apply a constrictive action to the teat to "milk" the same. Simultaneously, suction is constantly applied directly to the teat to draw off any milk forced therefrom by the foregoing cyclical constrictive action of the flexible sleeve.

The foregoing intermittent expansion and constriction action of the sleeve is an attempt to duplicate the manipulative actions of a person milking by hand. However, in most circumstances, for dairies utilizing an automatic milking system, it is still a requirement for a worker to finish milking the cow manually at the end of the automatic milking cycle to extract any remaining milk in the udder. This latter hand milking step is known in the jargon of the trade as "stripping" and is necessary to inhibit the development of mastitis and other diseases in cows associated with their failing to be properly milked. This latter step is also particularly important to assure suitable stimulation for continued lactation.

In view of the foregoing, what is needed is an apparatus and method for stimulating lactation in human females involved in breast feeding. It would also be an advancement in the art with respect to automatic milking devices in the dairy industry to provide an apparatus which improves the extraction of milk and minimizes the requirement for manual stripping of each individual cow at the conclusion of the milking process. Desirably, the milking apparatus and method should most closely approximate the suckling action of an infant and/or a nursing calf. Such an apparatus and method is disclosed and claimed in the present invention.

BRIEF SUMMARY AND OBJECTS OF THE INVENTION

The present invention provides a novel apparatus and method for closely approximating the natural suckling action of an infant to thereby stimulate lactation. The apparatus includes an inflatable collar which is placed in encircling engagement of at least the nipple portion of the mammary gland. Upon inflation, the inflatable collar imparts a constrictive action to the nipple and the underlying mammary gland adjacent the nipple. The constrictive action closely approximates the osculatory movements of the suckling infant. Furthermore, the collar structure of this invention may be suitably modified with inflatable compartments and/or a selectively controlled thickness along the inner face of the structure. The inflatable compartments mimic the oral movements of the infant while the variable wall thickness provide, upon inflation, a sequentially distending surface to impart a peristaltic pumping action to the mammary gland and nipple. The apparatus and method of this invention further includes means for selectively manipulating either the suction means or the inflation means of the structure to obtain the desired suction and/or stimulatory manipulative action of the apparatus, respectively.

It is, therefore, an object of this invention to provide improvements in the art of milking apparatus.

Another object of this invention is to provide an improved milking apparatus whereby a stimulative, manipulative action is imparted to the nipple and adjacent mammary gland.

Another object of this invention is to provide a milking apparatus which selectively combines suction and manipulative constrictive action to the nipple and mammary gland for improved lactation.

Another object of this invention is to provide an improved method for stimulating lactation.

These and other objects and features of the present invention will become more fully apparent from the following description and appended claims taken in conjunction with the accompanying drawing.

DETAILED DESCRIPTION OF THE PREFERRED EMBODIMENTS

The invention is best understood by reference to the Figures wherein like parts are designated with like numerals throughout.

General Discussion

Lactation is primarily a response to a lactogenic hormone of the pituitary gland, but is also influenced by the nervous system through the stimulus of suckling. Suckling involves the application of suction to the apertures of the lactiferous ducts in the end of the nipple while, simultaneously, imparting an oral or mechanical manipulation to the nipple and surrounding areola. Continued lactation is largely dependent upon the appropriate stimulation through suckling. Cessation of suckling over an extended period results in a temporary engorgement of the mammary gland with milk followed by a marked decrease in milk production. It is, therefore, customary for a nursing mother to mechanically apply suction to the breast to extract milk whenever the infant is ill or otherwise unable to suitably supply the necessary suckling activity.

With respect to the dairy industry, the hand-milking of a cow involves the milker or person doing the milking grasping the individual teat while pulling and squeezing downwardly in a rhythmic, peristaltic pumping action. The peristaltic pumping action occurs from the individual fingers being successively constricted around the teat from the index finger downwardly toward the little finger. In the absence of such manipulation, the mere application of suction generally proves to be unsatisfactory to suitably stimulate lactation, as is clearly recognized in the dairy industry.

Figure 8:
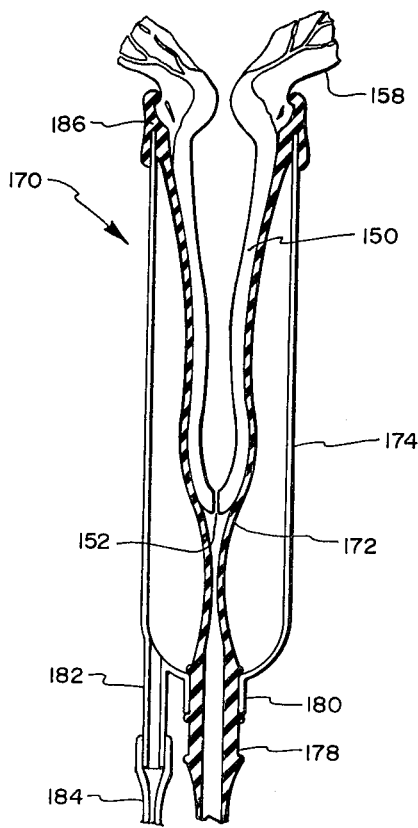
FIG. 8 is a cross section of a prior art dairy device shown schematically in the environment of a teat.

The functioning of the prior art milking device may be more easily understood with particular reference to FIG. 8 wherein one prior art device is shown generally at milker 170. Milker 170 includes a rigid housing 174 into which an elastic sleeve 172 is inserted. Sleeve 172 is formed from a natural rubber or other suitably elastic, flexible material. Sleeve 172 is referred to in the trade by the misnomer "inflation", although sleeve 172 is not inflatable, per se, but is distended outwardly toward the interior surface of housing 174 by the application of a negative pressure therebetween. The outward distension of sleeve 172 permits an engaged teat, teat 150, to expand outwardly and thereby allow milk to flow downwardly into teat 150. Release of the partial vacuum causes sleeve 172 to collapse about teat 150 resulting in a squeezing action to force some of the milk therein through the lactiferous duct 152. A continuous suction is applied to milk conduit 178 so as to draw off the resulting milk extracted from teat 150. The necessary negative pressure is supplied by a vacuum line 184 attached to a vacuum tube 182. The partial vacuum supplied through vacuum tube 184 is cyclically controlled so as to accommodate a periodic distension of sleeve 172.

This prior art device is completed by an annular collar 186 which surrounds the base of teat 150 and forms a seal between housing 174 and the basal periphery of teat 150. The lower end of sleeve 172 passes through a collar 180 in the base of housing 174 in a tight, sealing relationship.

It should be particularly noted that this prior art device does not accommodate any type of peristaltic pumping action. Instead, an essentially contrary pumping action is obtained whereby the squeezing action is first imparted to teat 150 near its lower end and progresses upwardly thereby forcing a substantial quantity of the milk in teat 150 upwardly also instead of downwardly and out through lactiferous duct 152.

Figure 1:
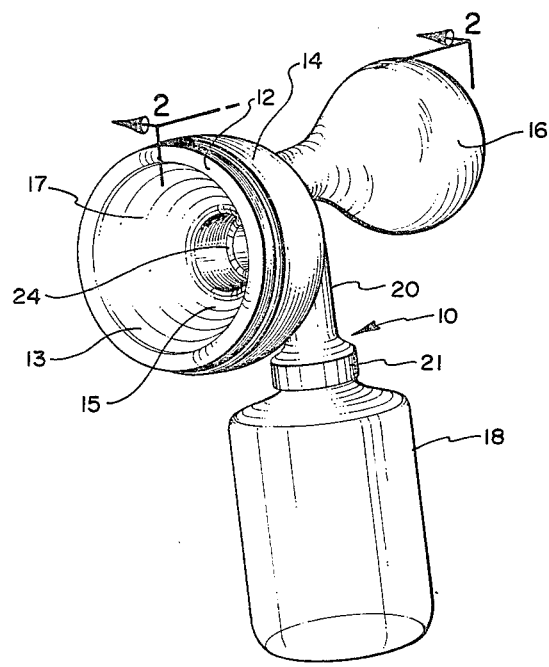
FIG. 1 is a perspective view of a first preferred embodiment of the milking apparatus of this invention.
Figure 2:
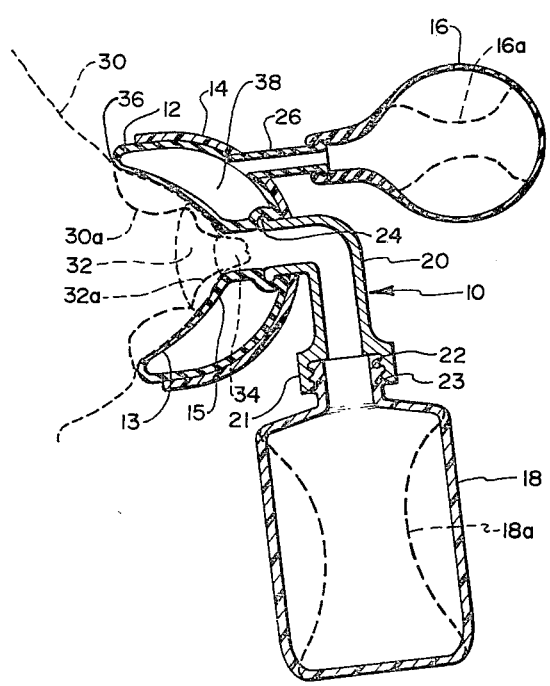
FIG. 2 is a cross section taken along lines 2—2 of FIG. 1 and shown schematically in the environment of a mammary gland.

Referring now more particularly to FIGS. 1 and 2, a first preferred embodiment of the lactation apparatus of this invention suitable for use by human females is illustrated herein generally at 10. The structure of lactation apparatus 10 includes a toroidal, inflatable collar 12 nested within a rigid housing 14. Housing 14 is rigid so as to inhibit the outward distension of collar 12 during inflation of the same. Collar 12 is formed as an inflatable member with a lumen 38 receiving air pressure from a squeeze bulb 16. Squeeze bulb 16 is selectively used to inflate collar 12 and thereby impart a manipulatory action to the underlying areas of a breast 30 (shown schematically in broken lines) as will be discussed more fully hereinafter.

Collar 12 is fabricated from a flexible rubber-like material and is formed in a toroidal configuration having a generally frusto-conical inner surface 17. Surface 17 is adapted to be placed in juxtaposition to breast 30 and in surrounding relationship to nipple 34. Surface 17 is fabricated from an expandable material which accommodates being distended by increased air pressure in lumen 38. Surface 17 preferably includes a preselected variation in thickness between an outer face 13 and an inner face 15. The preselected thickness variation of surface 17 accommodates a sequential distension of surface 17 upon inflation of lumen 38. In particular, outer face 13 is thinner so that it is more easily distended upon inflation of collar 12. Increased inflation pressure in collar 12 and, more particularly, lumen 38 causes surface 17 to distend progressively starting from between outer face 13 and extending toward inner face 15. This progressive distension imparts a constrictive action against breast 30 in a direction successively toward nipple 34 to thereby obtain a peristaltic pumping action on breast 30. This distension of surface 17 and the underlying manipulatory action imparted to breast 30 is illustrated schematically at broken lines 30a and 32a.

The schematic illustration herein representing the manipulation of breast 30, broken lines 30a and 32a, is shown as two essentially separate functions. This is easily accomplished by fabricating surface 17 in such a manner so as to obtain the selective manipulative effects illustrated. However, surface 17 is, preferentially, provided with the previously discussed graduated change in thickness between outer face 13 and inner face 15 to accommodate a continuous, smooth peristaltic manipulation of breast 30 in a direction toward nipple 34.

Selectively, surface 17 may also be configured to provide the inward distension as indicated by broken lines 30a by the novel technique of configurating lumen 38 into at least two interconnected compartments. Each compartment is formed by a lateral septum (hidden) on each side of lumen 38. These lateral septa would then cause the upper and lower faces of surface 17 to distend inwardly against breast 30 as indicated by broken lines 30a and thereby closely duplicate the upper and lower lip movements of a suckling infant (not shown).

Milk reservoir 18 is connected in fluid communication to nipple 34 in sealing relationship through a conduit 20 which is sealed to collar 12 along an annular bead 24. Milk reservoir 18 is removably secured to conduit 20 at union 21 by means of mating threads 22 and 23. Advantageously, milk reservoir 18 is fabricated with flexible side walls to accommodate being compressed as indicated at broken lines 18a and, upon release, drawing suction against nipple 34. Suction is maintained as long as a seal, indicated herein as seal 36, between breast 30 and collar 12 is suitably maintained or until the evacuated volume of milk reservoir 18 is filled with milk (not shown) ejected from the lactiferous ducts of nipple 34.

In operation, this first preferred embodiment of milking apparatus 10 is used by squeezing milk collection reservoir 18 to a position indicated by broken lines 18a. The inflatable collar 12 forms a seal 36 around nipple 34, areola 32 and the adjacent portions of breast 30. Thereafter, the flexible side walls of milk collection reservoir 18 are released to impart a continuous suction to at least nipple 34. Simultaneously and/or subsequently, squeeze bulb 16 is cyclically compressed as indicated at broken lines 16a to selectively inflate lumen 38 to impart the peristaltic manipulatory milking action to breast 30 as indicated at broken lines 30a and 32a. Additionally, broken lines 30a may also indicate the foregoing suckling action obtained by forming lumen 38 into at least two interconnected compartments by the foregoing lateral septa therein as set forth previously. Surprisingly, this combination of suction and manipulatory action imparted to the breast has been found to significantly improve lactation. Importantly, users of the apparatus of this invention have reported a significant increased lactation with surprisingly comfortable application and no resulting soreness, tenderness, or the like.

Figure 3:
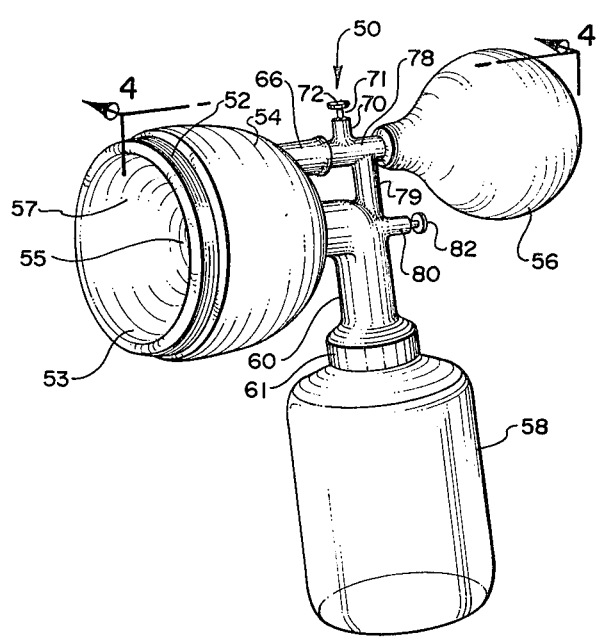
FIG. 3 is a perspective view of a second preferred embodiment of this invention.
Figure 4:
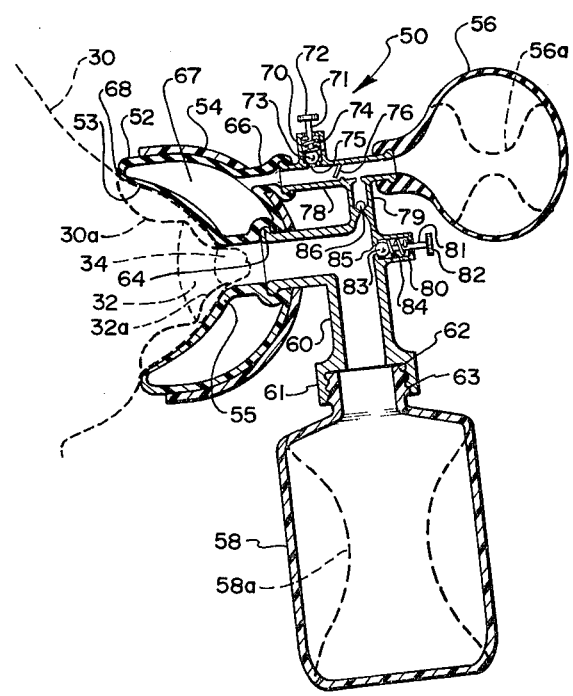
FIG. 4 is a cross section taken along lines 4—4 of FIG. 3 and shown schematically in the environment of a mammary gland.

Referring now more particularly to FIGS. 3 and 4, a second preferred lactation apparatus is shown generally at 50 and includes an inflatable collar 52 nested within a rigid housing 54. Rigid housing 54 is fabricated and functions similarly to housing 14 (FIGS. 1 and 2). Rigid housing 54 inhibits inflatable collar 52 from distending outwardly. Collar 52 includes a surface 57 which distends inwardly to thereby selectively constrict the underlying portions of a breast 30 as will be discussed more fully hereinafter and as set forth hereinbefore with respect to the embodiment of FIGS. 1 and 2. Inflatable collar 52 is fabricated substantially similar to inflatable collar 12 (FIGS. 1 and 2) and includes a hollow, toroidal lumen 67 which receives air pressure from a squeeze bulb 56. Additionally, lumen 67 may also be configurated as is lumen 38 (FIG. 2) with at least two laterally disposed septa (hidden) which form interconnected compartments in lumen 67. These septa inhibit distension of the overlying wall portions of internal face 57 to thereby provide a selective upper and lower distension of face 57 as indicated at broken lines 30a.

Squeeze bulb 56 is interconnected with inflatable collar 52 through a conduit 78. Conduit 78 is connected to a tubing 66 formed as an integral part of inflatable collar 52. Conduit 78 is also interconnected in fluid communication through a second conduit 79 with a milk conduit 60. A milk collection reservoir 58 is interconnected with milk conduit 60 at union 61.

A pair of one-way valves, valves 76 and 86, suitably control the direction of air pressure within conduits 78 and 79, respectively, so as to provide the suitable air pressure in lumen 67 and vacuum in milk conduit 60. For example, squeezing squeeze bulb 56 to the position indicated by broken lines 56a opens valve 76 and closes valve 86 thereby forcing air through conduit 78 into lumen 67. The air pressure in lumen 67 distends inflatable collar 52 inwardly as will be discussed more fully hereinafter.

Release of squeeze bulb 56 creates a suction in conduit 78 automatically closing valve 76 and opening valve 86. The suction thus created partially evacuates milk conduit 60 and milk collection reservoir 58. This partial evacuation imparts a partial suction against nipple 34. Additional suction against nipple 34 may be obtained by selectively collapsing the flexible walls of milk collection reservoir 58 to the position indicated in broken lines at 58a. Upon releasing the side walls of reservoir 58, suction is imposed against nipple 34 in a manner substantially similar to the functioning of milk collection reservoir 18 (FIGS. 1 and 2).

Manually operated pressure control valves 70 and 80 are contained in each of conduits 78 and 60, respectively, for the purpose of suitably adjusting the degree of pressure and partial vacuum, respectively, in each of said conduits. Valve 70 is configurated with a valve stem 71 to which a cap 72 is affixed at one end and a valve body 73 is affixed at the other end. A spring 74 is placed in valve 70 to force valve body 73 against a valve seat 75 to maintain pressure within conduit 78. Hand-grasping of cap 72 and forcing valve body 73 upwardly against spring 74 allows air pressure in conduit 78 to escape through valve 70.

Valve 80 is configured substantially similar to valve 70 and includes a valve stem 81 interconnected between a cap 82 and a valve body 83. Spring 84 presses valve body 83 against valve seat 85. Valve 80 is specifically adapted to accommodate release of any partial vacuum within milk conduit 60 and milk reservoir 58 by grasping cap 82 and lifting valve body 83 from valve seat 85. Additionally, valve 80 could be fabricated readily as an automatic vacuum release valve so as to allow air to enter conduit 60 and, more particularly, milk reservoir 58 in the event an excessive negative pressure is developed therein. For example, by reversing the relationship between valve body 83 and valve seat 85 and modifying spring 84 so as to pull valve body 83 against valve seat 85, valve 80 will automatically release the negative pressure when the strength of spring 84 is overcome thereby. Additionally, in the event an excessive partial vacuum develops within milk collection reservoir 58, valve 80 may be selectively opened to release part or all of the partial vacuum therein.

Although it is desirable to have a continuous suction on nipple 34, the apparatus of this invention provides improved lactation primarily by means of a cyclical inflation/deflation of inflatable collar 52. Accordingly, excessive air pressure within lumen 67 is released by opening valve 72. The inflation/deflation of collar 52 cycle is repeated by compressing squeeze bulb 56 to force air pressure into lumen 67. Release of squeeze bulb 56 draws a partial vacuum against nipple 34 as set forth hereinbefore. Selectively, this cyclic procedure can be repeated to the desired degree to obtain the appropriate manipulation of breast 30 and, more particularly, the underlying areas thereof while, simultaneously, imposing a partial vacuum against nipple 34.

Importantly, internal face 57 of inflatable collar 52 is fabricated from a flexible, elastic material. Face 57 is selectively fabricated with a thinner, outer periphery or wall 53 and graduates to a thicker, inner periphery or wall 55. In this manner, air pressure within lumen 67 selectively discends the thinner, outer wall 53 until it encounters sufficient resistance by its constriction of breast 30. The increasing air pressure in lumen 67 is then sufficient to also distend the inner wall face 55. In this manner, a peristaltic-type pumping action is selectively imparted to breast 30 beginning at the basal periphery represented by wall 53 and working toward the nipple periphery represented by wall 55. This sequential constriction of breast 30 is indicated schematically at broken lines 30a and 32a. This schematic illustration is shown herein as a two-step procedure although, clearly, in most likelihood, the peristaltic constriction of breast 30 would be a continuous movement from wall 53 toward wall 55. This combined suction and manipulatory action closely mimics the suckling action of an infant for a surprisingly improved lactation of breast 30.

Figure 5:
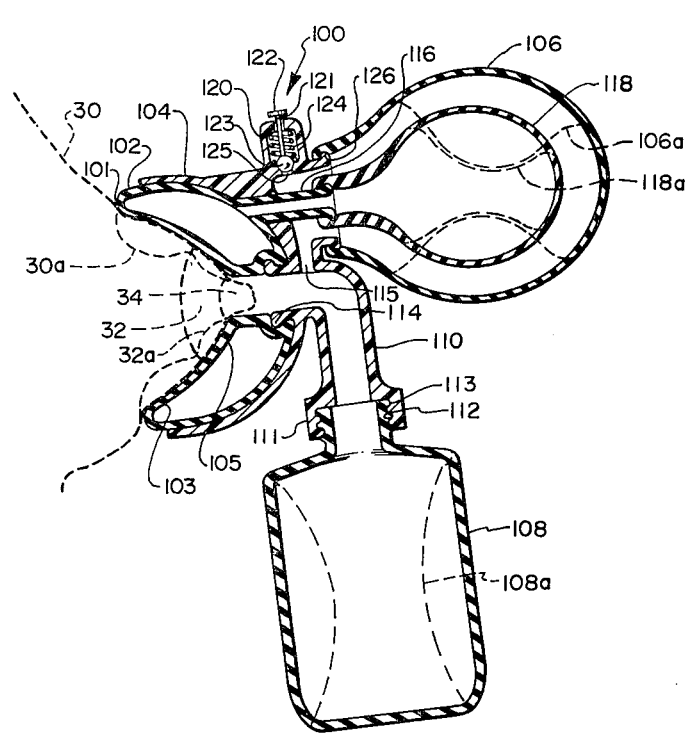
FIG. 5 is a cross section of a third preferred embodiment of this invention shown schematically in the environment of a mammary gland.

Referring now more particularly to FIG. 5, a third preferred lactation apparatus is shown generally at 100 and includes a double squeeze bulb configuration, squeeze bulbs 106 and 118. Lactation apparatus 100 also includes an inflatable collar 102 nested within a rigid housing 104. Rigid housing restricts the outward distension of collar 102 and is thereby fabricated so as to function similarly to rigid housing 14 (FIGS. 1 and 2) and rigid housing 54 (FIGS. 3 and 4).

Inflatable collar 102 is adapted to be placed in sealing relationship against a breast (shown schematically at broken lines 30) and in encirclement of areola 32 and nipple 34 to form a seal 101. Inflatable collar 102 is also configured and functions similarly to collar 12 (FIGS. 1 and 2) and collar 52 (FIGS. 3 and 4). Inflatable collar 102 may also be fabricated similarly to collar 12 (FIGS. 1 and 2) and collar 52 (FIGS. 3 and 4) by the inclusion of septa therein which configurate the lumen thereof into at least two interconnected chambers. The septa thereby provide the previously discussed distension features and which may be considered as being indicated schematically at broken lines 30a and 32a. Collar 102 is inflated upon compression of squeeze bulb 118 which is interconnected to collar 102 through conduit 116.

The second squeeze bulb, suction bulb 106, is interconnected in fluid communication to milk reservoir 108 through conduit 115. Suction bulb 106 readily accommodates the evacuation of milk collection reservoir 108 so as to provide the desired degree of suction against nipple 34. Additionally, reservoir 108 may be configurated similarly to reservoir 18 (FIGS. 1 and 2) and reservoir 58 (FIGS. 3 and 4) so that compression of its side walls, as indicated at broken lines 108a, and subsequent release will impart additional suction against nipple 34.

A valve 120 is interposed into the system to allow the operator (not shown) to release the partial vacuum in milk collection reservoir 108. Valve 120 includes a valve cap 122 interconnected to a valve body 123 by a valve stem 121. A compression spring 124 holds valve body 123 against a valve seat 125 until cap 122 is raised upwardly to permit air to rush inwardly into milk collection reservoir 108.

In operation, lactation apparatus 100 is placed over nipple 34 and areola 32 of breast 30 with inflatable collar 102 engaging breast 30 in sealing relationship around at least nipple 34 as indicated at seal 101. Thereafter, squeeze bulbs 106 and 118 are both squeezed to the positions indicated in broken lines 106a and 118a, respectively. The squeezing of squeeze bulb 118 forces air pressure into inflatable collar 102 to thereby impart the desired peristaltic pumping action to breast 30 as will be discussed more fully hereinafter. The air pressure developed within milk collection reservoir 108 by the squeezing of squeeze bulb 106 is released by opening valve 120.

The sequential release of squeeze bulbs 118 and 106 deflates inflatable collar 102 to its original position and imposes a partial vacuum on milk collection reservoir 108, respectively. Repetition of the foregoing manipulation of squeeze bulbs 106 and 118 develops a continuous partial vacuum within milk collection reservoir 108 and, correspondingly, on nipple 34. The suitable manipulation of squeeze bulb 118 selectively inflates and deflates inflatable collar 102 to thereby selectively manipulate the underlying portions of breast 30. This manipulatory action closely mimics the suckling action of an infant to thereby provide an improved lactation of breast 30.

If desired, squeeze bulb 106 may be maintained in a partially collapsed state against squeeze bulb 118. In this manner, squeeze bulb 118 and, correspondingly, the inflation/deflation of collar 102 may be cyclically repeated without developing undue partial vacuum pressures in milk collection reservoir 108. This third preferred lactation apparatus 100 is specifically configurated to be operated by one hand so as to allow the user greater freedom while undergoing lactation stimulation by the apparatus and method of this invention.

Figure 6:
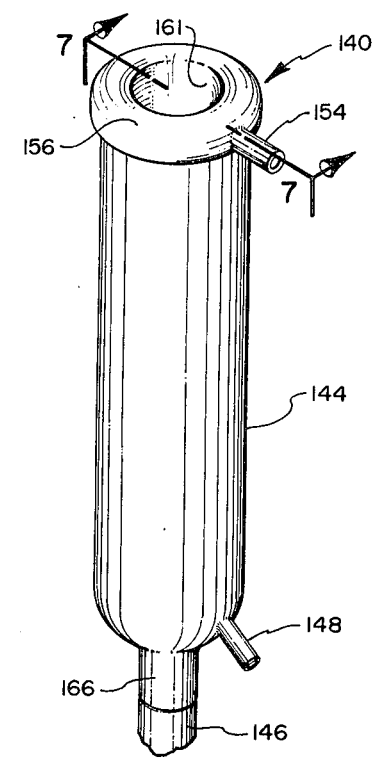
FIG. 6 is a perspective view of a modification of this invention to adapt it for use in the dairy industry.
Figure 7:
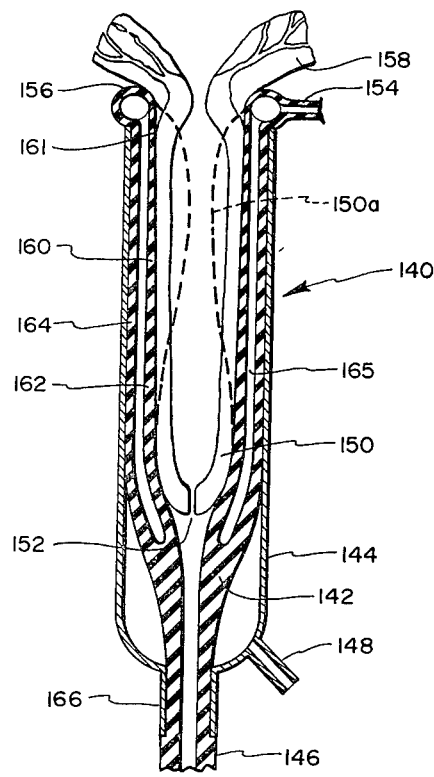
FIG. 7 is a cross section taken along lines 7—7 of FIG. 6 and shown schematically in the environment of a teat.

Referring now more particularly to FIGS. 6 and 7, a fourth preferred embodiment of the apparatus and method of this invention is illustrated herein as lacatation apparatus 140. Lactation apparatus 140 is particularly adapted for use in the dairy industry and includes a cylindrical shell 144 into which an inflatable sleeve 142 is inserted. Importantly, inflatable sleeve 142 is configurated as a double-walled sleeve having an inner wall 160 and an outer wall 164 forming therebetween an annular lumen 165. Air pressure is forced into lumen 165 to thereby distend wall 160 inwardly substantially similar to inflatable collars 12 (FIGS. 1 and 2), 52 (FIGS. 3 and 4), and collar 102 (FIG. 5).

Shell 144 is configurated substantially as the prior art shell 174 (FIG. 8) and includes a yoke 166 and a vacuum line connection 148. Inflatable sleeve 142 nests within shell 144 and has a downwardly depending conduit 146 engaged in sealing relationship with yoke 166. The upper end of inflatable sleeve 142 is also engaged in sealing relationship with the upper end of shell 144 in sealing relationship to thereby accommodate the imposition of a partial vacuum between shell 144 and the inflatable sleeve 142. The partial vacuum draws sleeve 142, including inner and outer walls 160 and 164, respectively, outwardly against shell 144 to thereby accommodate the appropriate distension of teat 150 engaged thereby. Additionally, vacuum is also drawn on line 154 to collapse lumen 165 thereby enlarging the volumetric condition of insert 142. A continuous partial vacuum is imposed on the interior of tube 146 so as to draw away milk ejected through lactiferous duct 152 from teat 150.

In operation, inflatable sleeve 142 is placed within shell 144 and suitably interconnected with the appropriate vacuum lines for vacuum connection 148, pressure line 154 and tube 146. A pressure line is also interconnected with pressure line 154 to suitably inflate inflatable sleeve 142 as will be set forth more fully hereinafter. A partial vacuum is drawn on vacuum connection 148 and simultaneously on pressure line 154 to distend inflatable sleeve 142 outwardly against the inner wall of shell 144. The distended sleeve 142 is then placed upwardly in engagement with teat 150 until collar 156 is in engagement with the udder 158.

The milking cycle is commenced by releasing through pressure line 154 the partial vacuum imposed in lumen 165 while, simultaneously or selectively, forcing air pressure through pressure line 154 into lumen 165. Outer wall 164 is held outwardly into engagement with the rigid wall of housing 144 by the partial vacuum on line 148 and the pressure in lumen 165. Correspondingly, the inner wall 160 is distended inwardly by the air pressure in lumen 165 as indicated in broken lines 150a so as to suitably constrict at least the upper portion of teat 150 to force milk therefrom through lactiferous duct 152. Release of the partial vacuum from vacuum connection 148 assists in the extraction of milk from the lower extremity of teat 150 by the combined action of air pressure in lumen 165 and the elasticity of insert 142. This latter step "strips" residual milk from teat 150. A partial vacuum is reapplied to vacuum line 148 and, selectively and/or simultaneously, to pressure line 154 to again open inflatable sleeve 142 to accommodate the inrush of milk into teat 150. Thereafter, the foregoing sequence is repeated and teat 150 is selectively milked by the apparatus and method of this invention.

Improved lactation of teat 150 is obtained by commencing the inflation cycle of insert or sleeve 142 before the suction through vacuum line 148 is terminated. This causes the inwardly distended inner wall 160 to "pinch off" the milk-engorged teat 150 adjacent inner wall 161 and thereby significantly increase the volume of milk extracted from teat 150. The foregoing cyclical sequence provides a surprisingly improved lactation of teat 150 since a major portion of the milk therein is not forced upwardly into udder 158 as occurs with the prior art device of FIG. 8.

The inflatable sleeve 142 of this invention provides surprisingly improved milking action by reason of its vacuum/pressure/release cycle. This is believed to be a significant advancement over the prior art device with its vacuum/release cycle for the foregoing reasons.

Importantly, inflatable sleeve 142 and, more particularly, wall 160 is fabricated with a varying thickness between a thin wall 161 and a thicker wall 162. In this manner, thin wall 161 will be preferentially distended adjacent the base of teat 150. Continued increase of air pressure through pressure line 154 will sequentially distend flexible wall 160 downwardly toward the lactiferous duct 152 of teat 150 to thereby impart a downwardly, peristaltic pumping action for improved lactation. This particular peristaltic-type pumping action most closely approximates the manual milking action of a person's hand (not shown) or a suckling calf (not shown).

Additionally, inner wall 160 may be interconnected to outer wall 164 by means of a plurality of interconnecting septa to separate lumen 165 into at least two interconnected chambers. Accordingly, upon inflation, inner wall 160 distends inwardly in at least two generally opposed portions to thereby more closely mimic the normal suckling action of a calf.

In comparison with the prior art device of FIG. 8, the peristaltic pumping action is directed downwardly from the base of the teat toward the tip whereas in the prior art device of FIG. 8 the squeezing action of the inflation 172 generally tends to pinch off the middle of the teat as schematically illustrated (FIG. 8) and thereby force milk in both directions. The lactation apparatus 140 of this invention provides a surprisingly improved lactation for the dairy industry and is a particularly significant improvement over the prior art device of FIG. 8.

Throughout this application reference is made to inflation by means of air pressure. Clearly, however, inflation of the specified inflatable structure may be suitably attained by any suitable inflation medium such as air, gas, or liquid. Accordingly, the claims are not to be construed as being limited in scope by inflation with air only as the inflation medium.

The invention may be embodied in other specific forms without departing from the spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by a Unites States Letters Patent is:

1. A milking apparatus for extracting fluid from a human breast comprising:

a housing;

an inflatable collar nested within the housing, the inflatable collar being adapted to encircle at least the nipple portion of the human breast, said collar comprising an inflatable toroid member, the toroid member comprising a generally concave annular wall surface facing away from the housing, the annular wall surface being readily distensible, the concave annular wall surface accomodating engagement with the human breast in encirclement of the nipple portion of the human breast, the annular wall surface being readily distended upon inflation of the toroid member to thereby impart a constrictive movement to the portion of the human breast engaged by the annular wall surface;

a fluid collection reservoir in fluid communication with the housing and accomodating fluid communication with the nipple portion encircled by the inflatable collar; and an inflation means connected to the inflatable collar to thereby accomodate imparting a constrictive movement to at least the nipple portion of the human breast upon inflation of the inflatable collar, the inflation means comprising at least two squeeze bulb means comprising a first squeeze bulb inside a second squeeze bulb, compression of the second squeeze bulb expelling air from the reservoir and allowing compression of the first squeeze bulb to direct the inflation of the inflatable collar inwardly against the human breast to thereby initate the suckling action of a nursing infant while release of the second squeeze bulb imparts a partial vacuum against said nipple.

2. A milking apparatus comprising:

a substantially rigid housing comprising a curvilinear shell and having an opening therethrough;

a reservoir means;

means coupling the opening through the housing to the interior of the reservoir;

an inflatable collar means having one surface thereof fitted within the curvilinear contour of the housing and defining a central opening aligned with the opening through the housing, said inflatable collar means having a resilient, breast-engaging, generally concave surface smoothly curved to generally conform to the surface of a breast of a lactating woman; and means for sequentially inflating and deflating said collar comprising a squeeze bulb, a first passage connecting the reservoir with the squeeze bulb, a first check valve means in the first passage to prevent flow from the squeeze bulb to the reservoir, and allowing flow from the reservoir to the squeeze bulb, a second passage connecting the squeeze bulb with said collar, second check valve means in the second passage permitting flow from the squeeze bulb to the collar while preventing reverse flow, and the means for sequentially inflating and deflating further including valve means connected between the interior of the collar and the outside atmosphere for controlling the pressure in the collar.

* * * * *